US007435380B2

(12) United States Patent
Winston

(10) Patent No.: US 7,435,380 B2
(45) Date of Patent: Oct. 14, 2008

(54) PSEUDO-PLASTIC OR THIXOTROPIC LIQUID DEODORANT PRODUCT FOR OSTOMY POUCHES

(75) Inventor: Anthony E. Winston, Brunswick, NJ (US)

(73) Assignee: Church & Dwight Co., Inc., Princeton, NJ (US)

( * ) Notice: Subject to any disclaimer, the term of this patent is extended or adjusted under 35 U.S.C. 154(b) by 1135 days.

(21) Appl. No.: 10/262,202

(22) Filed: Sep. 30, 2002

(65) Prior Publication Data

US 2004/0062681 A1 Apr. 1, 2004

(51) Int. Cl.
*A61L 9/00* (2006.01)
*A61L 9/01* (2006.01)
*B01D 11/02* (2006.01)
*A61K 49/00* (2006.01)
*A61K 38/28* (2006.01)
*A01N 25/00* (2006.01)
*C09K 3/22* (2006.01)
*C09K 3/00* (2006.01)
*A61M 1/00* (2006.01)
*A61F 5/44* (2006.01)

(52) U.S. Cl. ............... 422/27; 422/1; 422/5; 422/28; 422/261; 422/292; 422/300; 424/9.31; 424/76.1; 424/76.8; 424/78.26; 424/617; 424/722; 424/76.5; 424/76.3; 424/600; 424/78.08; 424/404; 424/405; 424/449; 424/423; 252/186.1; 252/88.2; 252/187.29; 252/192; 524/491; 524/848; 524/904; 524/770; 514/4; 514/154; 514/263.31; 514/491; 514/492; 514/970; 428/144; 428/381; 604/258; 604/259; 604/360; 604/368; 604/903; 604/317; 604/382; 604/333; 604/48

(58) Field of Classification Search ............... 422/1, 422/5, 28, 261, 292, 300; 424/9.31, 76.1, 424/76.8, 78.2, 617, 722, 76.5, 76.3, 600, 424/78.08, 404–405, 449, 423; 252/186.1, 252/88, 187.29, 192, 9.31, 76.1, 76.8, 78.26, 252/617, 722, 76.5, 76.3, 600, 78.08, 404–405, 252/449, 423; 524/491–492, 848, 904, 770, 524/949, 4, 154, 263.31, 970; 514/770, 949; 428/144, 381; 604/258–360, 368, 903, 317, 604/382, 333; 602/48

See application file for complete search history.

(56) References Cited

U.S. PATENT DOCUMENTS

| 3,755,598 | A | * | 8/1973 | Howe et al. .................. 514/523 |
| 3,767,586 | A | | 10/1973 | Rutkiewic ............... 252/187 H |
| 4,240,919 | A | * | 12/1980 | Chapman ................... 510/369 |
| 4,490,145 | A | | 12/1984 | Campbell .................. 604/333 |
| 4,648,882 | A | | 3/1987 | Osberghaus et al. ........... 8/142 |
| 4,704,222 | A | * | 11/1987 | Smith ........................ 510/396 |
| 4,740,366 | A | | 4/1988 | Winston et al. ............... 424/45 |
| 4,851,212 | A | | 7/1989 | Winston et al. ............... 424/45 |
| 4,873,000 | A | | 10/1989 | Weller ........................ 252/8.6 |
| 4,938,750 | A | | 7/1990 | Leise, Jr. .................... 604/333 |
| 5,005,520 | A | | 4/1991 | Michael ..................... 119/172 |
| 5,079,201 | A | | 1/1992 | Chu et al. ..................... 502/68 |
| 5,140,949 | A | | 8/1992 | Chu et al. ................... 119/174 |
| 5,534,249 | A | | 7/1996 | Maurer ...................... 424/76.3 |
| 6,010,666 | A | | 1/2000 | Kurokawa et al. .......... 422/122 |
| 6,015,547 | A | * | 1/2000 | Yam ........................... 424/49 |
| 6,025,074 | A | * | 2/2000 | Matsuo .................... 428/402.2 |
| 6,248,369 | B1 | * | 6/2001 | Nier et al. .................... 424/637 |
| 6,277,408 | B1 | | 8/2001 | Wellinghoff et al. ........ 424/473 |
| 6,296,841 | B1 | | 10/2001 | Schneider ................. 424/76.1 |
| 6,313,371 | B1 | | 11/2001 | Conant et al. ............... 604/389 |
| 6,333,054 | B1 | * | 12/2001 | Rogozinski ................. 424/661 |
| 6,420,312 | B2 | | 7/2002 | Nier et al. ................... 504/152 |
| 6,579,469 | B1 | * | 6/2003 | Nicholson et al. ....... 252/182.11 |

FOREIGN PATENT DOCUMENTS

GB 2 304 706 A 3/1997

\* cited by examiner

*Primary Examiner*—Jill Warden
*Assistant Examiner*—Monzer R Chorbaji
(74) *Attorney, Agent, or Firm*—Philli R. Kiefer; Frenkel & Associates; Stuart D. Frenkel

(57) ABSTRACT

A pseudo-plastic or thixotropic carrier having anti-malodorous components dissolved or suspended therein is sprayed on the internal surfaces of an ostomy bag or pouch. The viscoelastic properties of the carrier allow the composition to be conveniently dispensed from a spray bottle into the ostomy bag and retained on the inner walls thereof without being displaced therefrom by incoming waste during use of the ostomy bag. This allows the composition to continue to deodorize the ostomy bag headspace even after waste material begins to fill the bag.

9 Claims, No Drawings

PSEUDO-PLASTIC OR THIXOTROPIC LIQUID DEODORANT PRODUCT FOR OSTOMY POUCHES

CROSS-REFERENCE TO RELATED APPLICATIONS

Not Applicable

STATEMENT REGARDING FEDERALLY SPONSORED RESEARCH OR DEVELOPMENT

Not Applicable

FIELD OF THE INVENTION

The present invention relates to the field of deodorizers and particularly for deodorizers for use in or with ostomy bags. The invention further relates to pseudo-plastic or thixotropic compositions having deodorizing components dispersed or dissolved therein. The invention also relates to elimination of malodorous sulfur containing compounds typically found in or with fecal matter.

BACKGROUND OF THE INVENTION

Ostomy bags, by the very nature of their purpose, have malodors associated with their use. These malodors are typically due to sulfur containing compounds volatile compounds. As a practical matter, ostomy bags have been developed over time which direct gases that collect in the ostomy bag through deodorizing filters on the way to being released through one or more vents. A disadvantage of this type of deodorization system is that the deodorization only takes place for the very limited time that the malodorous gas is in contact with the filter as it traverses the filter as it leaves the ostomy bag. Also the filter has no deodorizing effect on the gases remaining in the ostomy bag above the fecal material and malodors are immediately released when the bag is opened for emptying.

Other ostomy bags have been developed in which a deodorizing material has been placed in a rupturable capsule which is contained inside the pouch and allows for the user to burst one or more of the capsules selectively. On release of the capsule contents, the deodorizing composition contained therein interacts with the contents of the ostomy bag to effect deodorization. One problem with this type of deodorization system is that the waste material entering the ostomy bag rapidly covers and dilutes the deodorizer which then can no longer effectively deodorize malodorous compounds in the gaseous headspace.

Many deodorizing formulations have been developed for addition to ostomy bags by the user. Most of these formulations are liquids which are added dropwise to the ostomy pouch prior to use. While these formulations may be chemically effective in neutralizing malodorous compounds, their actual efficacy in use is severely limited by the fact that fecal material subsequently enters the bag and covers the deodorizer, leaving an unreacted fecal surface, which continues to emit malodorous gases. There is therefore a need for more effective deodorants, which overcome these disadvantages.

OBJECTS OF THE INVENTION

It is among the objects of the present invention to provide an ostomy bag deodorizing product which continues to deodorize the headspace gases in the ostomy bag even after the incoming waste begins to fill the ostomy bag.

Another object of the invention is to provide an ostomy bag deodorizing product which provides for extended contact time with the headspace gas contained in the ostomy bag before that gas is released to the ambient atmosphere.

Yet another object of the invention is to provide an ostomy bag deodorizer product which is readily and easily applied by the ostomy bag user or care provider.

An even further object of the invention is to provide an ostomy bag deodorizer product which may be conveniently carried by the ostomy bag user or care provider for use anytime additional deodorization may be desired or needed.

Still other objects of the invention will be recognized by those of ordinary skill in the art.

BRIEF SUMMARY OF THE INVENTION

These objects are surprisingly achieved by a pseudo-plastic or thixotropic carrier having various deodorizing materials dissolved or suspended therein. The composition of the invention is sprayed on the internal surfaces of an ostomy bag or pouch. The viscoelastic properties of the carrier allow the composition to be conveniently dispensed from a spray bottle into the ostomy bag and retained on the inner walls thereof without being displaced therefrom by incoming waste during use of the ostomy bag. This allows the composition to continue to deodorize the ostomy bag headspace even after waste material begins to fill the bag. In addition, the headspace gas is in contact with the deodorizing composition for considerably longer times than the transit time through a filter in the pathway to an outlet vent.

BRIEF DESCRIPTION OF THE DRAWING

Not Applicable

DETAILED DESCRIPTION OF THE INVENTION

The present invention utilizes a pseudo-plastic or thixotropic liquid with deodorizing material suspended or dissolved therein. The kinetic viscosity of the pseudo-plastic or thixotropic liquid is very low, typically not more than about 2,000 cps, preferably not more than about 1,500 cps, more preferably not more than about 1,000 cps, still more preferably not more than about 500 cps, even more preferably, not more than about 100 cps, even still more preferably not more than about 50 cps, and most preferably not more than about 20 cps. The kinetic viscosity of the liquid has no minimum level, but typically is at least about 1 cps, more preferably at least about 2 cps. The low kinetic viscosity allows for the pseudo-plastic or thixotropic liquid (along with materials dissolved or dispersed therein) to be readily sprayed from a spray bottle or aerosol dispenser.

In contrast, the stationary viscosity of the pseudo-plastic or thixotropic liquid is quite high, typically at least about 10,000 cps, preferably at least about 15,000 cps, more preferably at least about 20,000 cps. While there is no required maximum for the stationary viscosity, it is typically not more than about 1,000,000 cps, more typically not more than about 500,000 cps, even more typically less than 300,000 cps. The larger stationary viscosity permits the composition, upon being deposited on the intended surface, to stay where deposited and not be dislodged or washed away from the surface on which it was deposited during ordinary conditions of use.

In the context of an ostomy pouch, the combined low kinetic viscosity and high stationary viscosity permit a user to dispense the composition from a spray or aerosol container onto the interior walls of the ostomy pouch and the composition so dispensed will stay in place without slipping down to the bottom of the bag during use. While some of the deodorizing composition may get washed down the sides of the bags due to contact with incoming fecal material, much of the deodorizer material remains in place above the waste to deodorize the headspace. Since the composition so dispensed contains deodorizing components, those components will continue to deodorize the headspace within the pouch above the collected waste matter even as waste matter washes over portions of the pouch walls. Preferably, this allows for a portion of the composition (including its deodorizing components) to remain out of contact with the waste matter (and as such avoid or minimize inactivation or absorption of the deodorizing components by the waste matter itself).

The pseudo-plastic or thixotropic liquid can be prepared from inorganic thickeners (primarily clays) or organic polymers or mixtures thereof, which produce pseudo-plastic solutions or suspensions when mixed with water. The most preferred thickeners are primarily the inorganic ones together with very minor amounts of organic thickeners. Inorganic thickeners suitable for use in preparing pseudo-plastic liquids of the invention include, but are not limited to, synthetic or natural thickening clays having particle sizes generally less than about 200 nm which clay has been externally reacted with a divalent, trivalent, or tetravalent metal cation. Preferably the clays are sodium magnesium silicate based and sodium lithium magnesium silicate based clays similar to hectorite. Particularly preferred are clays available as Laponite (Laporte Industries, Ltd, Cheshire, England) and Vee-Gum and Van Gel (Vanderbuilt Minerals Corp.). Other inorganic thickeners suitable for use in the invention include bentonite clays and calcium silicate. The clays are generally used in amounts of 2-6% of the deodorizer formulation. When clays are used for the present invention, they are thoroughly hydrated in water and then externally reacted with about $1\times10^{-5}$ moles to $2\times10^{-3}$ moles of divalent, trivalent, or tetravalent metal cation per gram of clay by addition of a salt of such metal cation to the aqueous carrier. The preferred divalent, trivalent, and tetravalent metal cations suitable for the external reaction with the clay include, without limitation calcium, magnesium, strontium, barium, zinc, copper, manganese and iron; even more preferably zinc, copper, and iron (II). Preferably the divalent, trivalent, and tetravalent metal cations are present in an amounts of a salt thereof at about $2\times10^{-5}$ moles to $1.67\times10^{-3}$ moles, more preferably $4\times10^{-5}$ moles to $8\times10^{-4}$ moles of such metal cation per gram of clay. Most preferably the clay used in the instant invention is Laponite at a concentration of 2 to 6% and which has been reacted (either previously or in situ in the preparation of the formulations of the present invention) with about 0.01 to about 0.3%, most preferably about 0.04% to about 0.1% copper ions by weight of the complete composition. A particular advantage of the inorganic thickener systems can be the production of gel-like consistencies which reduces the tendency for the product to leak out of its container when kept in a pocket or purse and thereby reduces the likelihood of damage to clothing etc.

Organic polymers suitable for use in preparing pseudo-plastic liquids of the invention include, but are not limited to, xanthan gum, carboxymethylcellulose (or its alkali metal salts), polyacrylates (preferably with a molecular weight in the range of 100,000 to about 2,000,000), guar gum, and sodium alginate. The most preferred gums are xanthan gum, gellan gum and iota carrageenan gum. When the organic polymers are used alone, they are used in amounts of from about 0.1 to 2.0%. When they are used as supplements to inorganic thickeners they are used at levels of 0.01% to about 0.2%, preferably about 0.02% to about 0.1%, more preferably about 0.04% to about 0.08% of the deodorizing composition. The organic polymers generally help to prevent syneresis and other compatible materials having an antisyneresis property are suitable as well.

The inorganic thickeners and organic polymers above are used in concentrations suitable to provide the viscosity ranges set out above. Typical formulations of the present invention comprise from 2 to about 6% (although up to about 10% can be used when desired), preferably about 3 to about 5%, most preferably about 4% inorganic thickener and generally not more than about 2%, preferably 0 to about 0.2%, more preferably about 0.01% to about 0.2%, still more preferably about 0.025 to about 0.1%, more preferably 0.04% to about 0.08%, most preferably about 0.05% organic polymer, provided that the maximum kinetic viscosity and minimum stationary viscosity limitations are above are adhered to.

In addition to the pseudo-plastic or thixotropic liquid detailed above, the compositions of the invention further comprise at least one deodorization active selected from fragrance; alkali metal bicarbonate; alkali metal carbonate; sulfur precipitating compound containing copper, zinc, silver, tin, bismuth, zirconium, strontium or iron; agents suitable for (a) oxidizing sulfides and other sulfur containing compounds or (b) otherwise chemically reacting with malodorant compounds or precursors present in human waste; bacteriocide; suspended absorbents such as activated carbon, clay or zeolites; enzymes; solvents for malodorant compounds. For these additional components, certain compounds, such as copper (II), zinc, etc, may serve multiple functions. For example, copper and zinc compounds may have sulfur precipitating capability and bacteriocidal properties. When such compounds potentially having multiple functions are present and the differing functions have different suitable or typical ranges for which those materials may be present, the compound may in fact be present up to the maximum amount indicated for any of the functions it may fulfill unless specifically stated herein otherwise. It should be noted that in many cases the heavy metals used for externally reacting with the inorganic thickener can also supply some deodorization and/or bactericidal efficacy, even at the low concentrations used. This is a particular of the advantage of using copper, zinc, strontium, manganese and iron salts as the external clay reactant. However, when inorganic clays are used as the thickener, the amount of polyvalent metal ion is limited. Excessive concentrations will lead to a breakdown in the formulation viscosity. The maximum polyvalent metal cation to be reacted with the particular clay can be readily determined by plotting (viscosity) vs. (polyvalent meal cation:clay) and determining the viscosity range desired for the particular application.

Further details concerning the externally reacted clay may be found in the Inventor's copending U.S. patent application Ser. No. 10/262,205, publication no. US 2004-0063796 A1, entitled High Ionic Strength Tolerant thickening Systems and Products Formulated therewith, filed simultaneously herewith and incorporated herein in its entirety.

Any alkali metal bicarbonate and any alkali metal carbonate are suitable for use in the present invention although the respective sodium and potassium salts are preferred and the respective sodium salts are most preferred (primarily due to cost factors). These materials are typically employed in amounts of from about 0.5 to about 5% but as much as 10% can be used where desired. Generally, the carbonate and bicarbonate salts are employed to neutralize short chain aliphatic acids (such as butyric acid and isovaleric acid) making then more soluble in the liquid contents and thereby less volatile.

Sulfur precipitating compounds which can react with hydrogen sulfide, methyl mercaptan and/or organic sulfides include those compounds containing copper, zinc, iron, bismuth, zirconium, strontium and silver. These compounds are used at concentrations between 0.1 and 5%, preferably 0.5 to 2%.

Further details concerning certain suitable chlorinating agents can be found in the Inventor's copending U.S. patent application Ser. No. 10/262,208, publication no. US 2004-0062742 A1, entitled Deodorant Product Containing Chlorinating Agents and Buffered Alkaline Salts, filed simultaneously herewith and incorporated herein in its entirety.

Suitable agents for oxidizing sulfur or otherwise reacting with malodorants or malodorant precursors in human waste suitable for use in the present invention include Chloramine-T, other chlorinating agents, peroxides, etc. These materials are utilized in amounts which would be equivalent in oxidizing potential of about 0.05% to about 5% hypochlorite ion.

Suitable bacteriocides to prevent new odor development include quaternary ammonium compounds such as benzalkonium chloride, phenol derivatives such as triclosan, etc. at concentrations of from about 0.05 to 1% of the formulation. Heavy metal salts such as copper, zinc, bismuth and silver salts can also be used as bactericides. Useful concentrations for these salts range from 0.01% to 3% based on the formulation.

Enzymes suitable for use in the present invention include, but are not limited to proteases, amylases, lipases, lysozymes, and cellulases. These materials, when present in the present invention formulations are present typically in amounts of from 0.1% to about 2% of the formulation.

Malodorous material solvents and other proprietary deodorizers, when used are generally used in amounts of about 0.5 to 5%, preferably 1 to 3% based on the formulation. These materials include propylene carbonate, propylene glycol, polypropylene glycol, polyethylene glycol, alkylene glycol alkyl ethers, alkoxy alkanols, Matazene® (Pestco Co), Odor Synthesis® (Shaw Mudge) and zinc ricinoleate.

Generally, the compositions of the present invention will include a chlorinating agent such as Chloramine-T. When the formulation does include such an agent, the other components used must be chlorine stable, especially fragrances. Those of ordinary skill in the art will undoubtedly be aware of chlorine stable materials for use in the present invention.

In addition, the compositions of the present invention may optionally include other formulation and processing aids including surfactants such as sodium lauryl sulfate, sodium lauroyl sarcosinate and sodium alkyl ether sulfonate at concentrations from about 0.05 to about 1% based on the formulation.

In general, the formulations of the invention are prepared by mixing the organic polymer (if used) with water (generally sprinkling it into water and mixing for at least about 15 minutes to obtain good hydration of the polymer. The clay is then hydrated in the water, preferably by heating it to from about 40° C. to about 80° C. preferably about 60° C. and rapidly mixing for from about 10 minutes to 2 hours preferably about 30 minutes. Optimum temperatures and mixing times may vary depending on the inorganic thickener used. While rapidly mixing, a solution containing about 1% to about 5% of a divalent, trivalent, or tetravalent metal cation salt, preferably a copper salt, more preferably copper sulfate or copper chloride, is added and the mixture is rapidly mixed for from about 5 minutes to 1 hour preferably about another 15 minutes. The mixture is then cooled to room temperature. The remaining ingredients are then added sequentially, generally in any convenient order.-After each of the additions, the mixture is again mixed (preferably blended) for about 2 minutes to about 30 minutes preferably about 5 minutes. The subsequent order of addition is not generally critical. However, when fragrance and surfactant are added, they are usually added last and the final mixing step after their addition should be for from about 2 minutes to 30 minutes preferably about 10 minutes.

EXAMPLES

The following examples exemplify, but do not limit, the present invention.

Examples 1-4

Pseudo-plastic formulations of the instant invention are set forth in the table below.

| Component | Ex. 1 Weight % | Ex. 2 Weight % | Ex. 3 Weight % | Ex. 4 Weight % |
|---|---|---|---|---|
| Water | 88.300 | 88.150 | 88.300 | 88.60 |
| VEEGUM | — | 4.000 | — | — |
| Laponite RD | 4.000 | — | 4.000 | 4.000 |
| Xanthan Gum | 0.050 | 0.050 | 0.00 | 0.000 |
| Chloramine-T | 2.000 | 2.000 | 2.000 | 2.000 |
| Copper Chloride Dihydrate (3.6%) | 2.400 | 2.400 | 2.400 | 2.400 |
| Na bicarbonate | 1.000 | 1.000 | 1.000 | 1.000 |
| Ca carbonate | 2.000 | 2.000 | 2.000 | 2.000 |
| Avanel S74 | — | — | 0.300 | — |
| Na lauryl sulfate | 0.050 | 0.200 | — | — |
| Fragrance | 0.200 | 0.200 | — | — |
| Total | 100.000 | 100.000 | 100.000 | 100.000 |

In each case, the Laponite or Veegum together with the xanthan gum are dispersed in the water in a high shear mixer. The dispersion is heated to 60° C. and stirred for 30 minutes. The mixture is then cooled to room temperature. The copper chloride is then slowly added and followed by 5 minutes of additional stirring. Next the sodium bicarbonate is added followed by 5 minutes of further stirring. Then the calcium carbonate is added, followed by 5 minutes of still more stirring. Then the Chloramine-T is added and followed by 5 minutes additional stirring. Next, if present, the Avanel S74 (a sodium alkyl ether sulfonate available from BASF) or sodium lauryl sulfate is added with an additional 5 minutes stirring. If fragrance is present, it is added with the surfactant and the entire mixture is stirred for 10 minutes.

The resulting compositions are placed into spray bottles and can be readily sprayed therefrom. The sprayed composition adheres to surfaces on which it is sprayed and remains where deposited despite the surface being held vertically. Another advantage of the above formulations is the non-liquid gel-like nature when in the spray bottles. This greatly reduces the potential for the product to leak from the container. The product can be supplied in small containers which can conveniently be kept in a pocket or purse with little risk of leakage and damage to clothing etc.

Examples 5-7

Additional Pseudo-plastic formulations of the instant invention are set forth in the table below.

| Component | Ex. 5 Weight % | Ex. 6 Weight % | Ex. 7 Weight % |
|---|---|---|---|
| Water | 94.00 | 91.20 | 96.500 |
| Xanthan Gum | 1.0 | 0.0 | 1.500 |
| Iota Carrageenan gum | 0.0 | 0.8 | 0.000 |
| Chloramine-T | 2.000 | 0.000 | 0.000 |
| Copper Citrate | 0.000 | 1.000 | 0.000 |
| Silver nitrate | 0.000 | 0.000 | 2.000 |
| Sodium citrate | 0.000 | 2.000 | 0.000 |
| Na bicarbonate | 1.000 | 1.000 | 0.000 |
| Calcium carbonate | 1.000 | 0.000 | 0.000 |
| Activated carbon | 0.000 | 4.000 | 0.000 |
| Zinc oxide | 1.000 | 0.000 | 0.000 |
| Total | 100.000 | 100.000 | 100.000 |

Example 8

A further pseudo-plastic formulation of the instant invention are set forth in the table below

| Component | Weight % |
|---|---|
| Water | 86.0 |
| Gellan Gum | 1.0 |
| Atapulgite clay | 4.0 |
| Na bicarbonate | 1.0 |
| Calcium peroxide | 4.0 |
| Zeolite | 4.0 |
| Total | 100.0 |

I claim:

1. A method of reducing malodors associated with use of an ostomy bag comprising applying to inner walls of an ostomy bag a composition comprising a pseudo-plastic or thixotropic liquid and at least one ostomy deodorizing compound dissolved or dispersed therein, wherein said pseudo-plastic or thixotropic liquid has a kinetic viscosity of not more than about 2,000 cps and a stationary viscosity of not less than 10,000 cps.

2. The method of claim 1 wherein said deodorizing compound comprises a chlorinating agent.

3. The method of claim 2 wherein said deodorizing compound is Chiloranime-T.

4. The method of claim 1 wherein said pseudo-plastic or thixotropic liquid comprises water and a carrier solid selected from the group consisting of inorganic thickeners, organic polymers, and mixtures thereof.

5. The method of claim 4 wherein said carrier solid comprises an inorganic thickener, said inorganic thickener is selected from the group consisting of sodium magnesium silicate, sodium lithium magnesium silicate, and mixtures thereof.

6. The method of claim 4 wherein said carrier solid comprises an organic polymer, said organic polymer is selected from the group consisting of xanthan gum, carboxymethylcellulose and its alkali metal salts, polyacrylates, guar gum, sodium alginate, Iota Carrageenan, Gellan gum and mixtures thereof.

7. The method of claim 4 wherein said inorganic thickener has a particle size of not greater than about 200 nanometers.

8. The method of claim 4 wherein said inorganic thickener is present in an amount of about 2% to about 10% of said composition.

9. The method of claim 4 wherein said organic polymer is present in an amount of about 0.01% to about 2% of said composition.

\* \* \* \* \*